United States Patent [19]

Quan et al.

[11] Patent Number: 5,254,695

[45] Date of Patent: Oct. 19, 1993

[54] SUBSTITUTED TRIAZOLES

[75] Inventors: Peter M. Quan, Rochdale; David Stewart, Royton; Anthony J. Nelson, Middleton, all of England

[73] Assignee: Imperial Chemical Industries PLC, London, England

[21] Appl. No.: 683,135

[22] Filed: Apr. 10, 1991

Related U.S. Application Data

[60] Continuation of Ser. No. 391,982, Aug. 10, 1989, abandoned, which is a division of Ser. No. 165,350, Feb. 29, 1988, Pat. No. 4,879,388, which is a continuation of Ser. No. 912,660, Sep. 29, 1986, abandoned, which is a continuation of Ser. No. 663,696, Oct. 22, 1984, abandoned.

[30] Foreign Application Priority Data

Nov. 17, 1983 [GB] United Kingdom ............... 8330715

[51] Int. Cl.$^5$ ............................................. C07D 249/08
[52] U.S. Cl. ................................................... 548/266.8
[58] Field of Search ............... 548/268.4, 266.8, 268.2, 548/268.6

[56] References Cited

U.S. PATENT DOCUMENTS

| | | | |
|---|---|---|---|
| 3,701,645 | 10/1972 | Scott | 71/1 |
| 3,843,667 | 10/1974 | Cupery | 548/341 |
| 4,576,815 | 3/1986 | Robinson | 423/658.5 |
| 4,581,220 | 4/1986 | Nelson | 423/658.5 |
| 4,584,008 | 4/1986 | Cherpeck | 71/76 |

FOREIGN PATENT DOCUMENTS

| | | |
|---|---|---|
| 0007010 | 1/1980 | European Pat. Off. . |
| 0010270 | 4/1980 | European Pat. Off. . |
| 0015502 | 9/1980 | European Pat. Off. . |
| 0112617 | 7/1984 | European Pat. Off. . |
| 1508153 | 6/1975 | United Kingdom ............. 548/268.4 |
| 1535777 | 12/1978 | United Kingdom ............... 548/262 |

OTHER PUBLICATIONS

Ruscoe, et al., CA89:38091f (1978).

Primary Examiner—Patricia L. Morris
Attorney, Agent, or Firm—Cushman, Darby & Cushman

[57] ABSTRACT

Metal values, especially copper values, are extracted from aqueous solutions of metal salts containing halide or pseudo halide ions by a 1,2,4 triazole substituted in the 1-position by (1) a hydrocarbyl (alkyl) group or (2) a group of the formula —$(X)_n$—$(CO-Y)_m$ where X is an optionally substituted methylene, vinylene or phenylene linking group or a linking group of formula —CO—A— where A is an optionally substituted aromatic ortho linking group; n is 0 or 1; Y is $OR_2$ or $R_3$ where $R_2$ and $R_3$ are hydrocarbyl groups containing from 5 to 36 carbon atoms (preferably branched alkyl groups containing from 9 to 24 carbon atoms); and m is from 1 to 3.

2 Claims, No Drawings

SUBSTITUTED TRIAZOLES

This is a continuation of application Ser. No. 07/391,982, filed on Aug. 10, 1989, which was abandoned upon the filing hereof which in turn is division of application 07/165,350, filed Feb. 29, 1988, now U.S. Pat. No. 4,879,388, which in turn is a continuation of application 06/912,660 filed Sep. 29, 1986, now abandoned, which in turn is a continuation of application 06/663,696, filed Oct. 22, 1984, now abandoned.

This invention relates to a process for the extraction of metal values from aqueous solutions of metal salts, and in particular to a process for the extraction of metal values from aqueous solutions in the presence of halide anions.

The use of solvent extraction techniques for the hydrometallurgical recovery of metal values from metal ores has been practised commercially for a number of years. For example copper may be recovered from oxide ores or from ore tailings by treating the crushed ore with sulphuric acid to give an aqueous solution of copper sulphate which is subsequently contacted with a solution in a water-immiscible organic solvent of a metal extractant whereby the copper values are selectively extracted into the organic phase.

The application of solvent extraction techniques to aqueous solutions containing halide anions however has presented numerous technical problems. For example copper bearing sulphur-containing ores such as chalcopyrite may be leached using ferric chloride or cupric chloride solutions, but the solvent extraction of the resultant leach solutions presents formidable difficulties.

The present invention provides a process for the extraction of metal values from aqueous solutions containing halide ions by the use of metal extractants whose several properties meet the stringent requirements imposed on the extractant by the system.

According to the present invention there is provided a process for extracting metal values from aqueous solutions of metal salts containing halide or pseudo halide anions which comprises contacting the aqueous solution with a solution in a water-immiscible organic solvent of a 1-substituted-1,2,4-triazole of formula:

where R is:
(1) a hydrocarbyl group, $R_1$, containing from 5 to 36 carbon atoms; or
(2) R is a group of the formula:

wherein X is an optionally substituted methylene linking group, an optionally substituted vinylene linking group, an optionally substituted phenylene linking group or a linking group of formula:

where A is an optionally substituted aromatic ortho linking group; and n is 1 or 0; and wherein Y is $OR_2$ or $R_3$ where $R_2$ and $R_3$ are hydrocarbyl groups containing from 5 to 36 carbon atoms and m is from 1 to 3.

When n in formula (2) is 0, m must be 1 and the triazoles of the present invention are 1-(hydrocarb)oxycarbonyl or 1-hydrocarboyl derivatives of respective formulae:

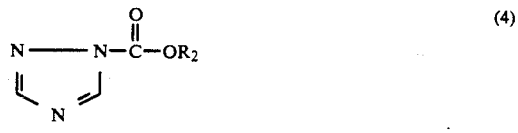

and

When n in formula (2) is 1 and X is a methylene group, the 1-substituted triazoles of the present invention have the formula:

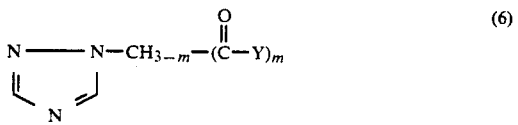

wherein m is from 1 to 3 and Y has the meaning given above, and wherein one or both of the —H atoms (if present) may be replaced by an optional substituent such as a halogen atom, cyano group, nitro group or lower alkyl group. We have found that when m is 3, the compounds generally have reduced hydrolytic stability, and it is preferred that m is 1 or 2. When m is 2, the compound of formula (6) is found to show a good balance of properties as between hydrolytic stability and reagent "strength" as discussed below.

The term "lower alkyl group" as used herein indicates an alkyl group containing from 1 to 4 carbon atoms.

When n in formula (2) is 1 and X is an optionally substituted vinylene linking group, the triazole of the present invention preferably has the formula:

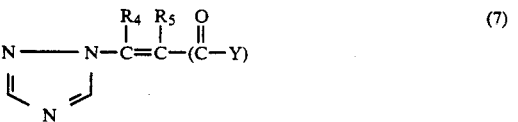

wherein Y has the meaning given previously and $R_4$ and $R_5$ are hydrogen or optional substituents such as a halogen atom (for example a fluorine or chlorine atom), cyano group, nitro group or a lower alkyl group or the group —CO.Y.

When n is 1 in formula (2) and X is a linking group of formula (3), the group —A— is preferably an optionally substituted ortho phenylene linking group. As optional substituents there may be mentioned halogen atoms, alkyl groups, cyano and nitro groups. It is especially preferred that there is present a substituent which provides steric hindrance in respect of the approach to the carbonyl group attached to the triazole ring, since we have found that such compounds generally have improved hydrolytic stability. Thus for example preferred groups X of formula (3) have the formula:

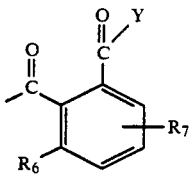 (8)

wherein $R_6$ is a halogen atom, a cyano group, a nitro group or an alkyl group (for example a lower alkyl group) and $R_7$ is hydrogen or one or more optional substituents, for example one or more halogen atoms.

The hydrocarbyl groups $R_1$, $R_2$ and $R_3$ in formula (1), are preferably alkyl groups, and preferably alkyl groups containing from 9 to 24 carbon atoms, for example octyl, nonyl, decyl, dodecyl, tridecyl, pentadecyl, hexadecyl or octadecyl groups or a higher alkyl group.

To achieve good solubility of the compound in preferred organic solvents, $R_1$, $R_2$ and $R_3$ respectively are preferably branched alkyl groups or a mixture (including an isomeric mixture) of branched alkyl groups. As will be discussed later, we have found that certain branched chain groups also provide improved hydrolytic stability.

Highly branched groups $R_1$ may be usefully derived from branched alcohols prepared by the Guerbet and Aldol condensations. Such alcohols are characterised by branching at the position beta to the hydroxyl group and have the general formula:

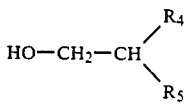 (9)

wherein $R_4$ and $R_5$ are both alkyl groups and $R_4$ contains two fewer carbon atoms than $R_5$. $R_4$ and $R_5$ may be straight chain or branched chain alkyl groups and may be isomeric mixtures of alkyl groups. A mixture of highly branched alcohols may be obtained by Guerbet or Aldol condensations of mixtures of alcohols and aldehydes respectively. By way of example, good solubility in preferred organic solvents is conferred on the triazole compounds wherein $R_1$, $R_2$ and $R_3$ respectively are derived from commercial isooctadecanol prepared to consist essentially of a mixture of geometrical isomers of the compound (formula 10):

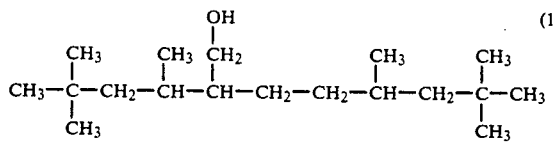 (10)

The 1-substituted triazoles of the present invention may be prepared by conventional means. For example the (hydrocarb)oxycarbonyl derivatives wherein, in formula (2), Y is $OR_2$ and n is 0 may be prepared by the reaction of a hydrocarbyl chloroformate, derived from the corresponding hydrocarbyl alcohol, $R_2OH$, with 1,2,4-triazole. If n is 1, the compounds may be prepared by reaction of the alcohol $R_2OH$ with the acid:

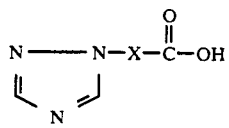

or with the acid anhydride thereof.

Hydrocarboyl derivatives wherein, in formula (2), Y is $R_3$ and n is 0 may be prepared by reaction of a carboxylic acid chloride, which may itself be prepared via oxidation of an alcohol, with the triazole. Thus the alcohol of formula $R_3CH_2OH$ may be used to provide the group Y whose formula (corresponding to formula (5)) is:

Note that in this instance the group $R_3$ has one less carbon atom than the starting alcohol $R_3CH_2OH$.

Hydrocarboyl derivatives wherein Y in formula (2) is $—R_3$ and n is 1 may be prepared by reaction of the chloride $R_3$—CO—X—Cl with the triazole.

We have found that compounds having a high degree of branching at the positions in the vicinity of the carbonyl group in formula (2) generally show an improved resistance to hydrolysis under the stringent conditions employed in the solvent extraction process.

For example for 1-(hydrocarb)oxycarbonyl derivatives wherein Y is $—OR_2$, a high degree of branching at the position in the vicinity of the carbonyl group may be obtained for example by using a secondary alcohol as starting material. Suitable secondary alcohols may be prepared for example by the procedures described by Pearce, Richards and Scilly in J. Chem. Soc. (Perkin I) pp 1655 to 1669. We have found for example that the product of Example 16, which is prepared from such a secondary alcohol, has even higher hydrolytic stability than the products of Examples 1, 2 and 3.

The process of the present invention may be applied to the extraction from aqueous solutions containing halide or pseudohalide ion of any metal capable of forming a stable halide or pseudohalide containing complex with the triazole in the water-immiscible organic solvent. Examples of such metals include copper, cobalt, cadmium and zinc. The process of the present invention is especially suitable for the solvent extraction of copper from aqueous solution obtained by the halide or pseudohalide leaching of sulphur containing ores, for example from solutions obtained by the leaching of ores such as chalcopyrite with aqueous ferric chloride or cupric chloride solutions.

It will be appreciated that the process of the present invention may be incorporated into a wide variety of different methods for the overall recovery of metals from their ores or from other metal-bearing sources. Details of these methods will vary depending on the metal concerned and the nature and composition of the leach solution. By way of example, an integrated process which is especially suitable for leach solutions containing high levels of cupric ion is described in European Patent Publication No. 57797.

A typical solvent extraction process for recovering copper from a sulphide or complex sulphide ore involves the following stages:

(1) Leaching of the copper ore with aqueous ferric or cupric chloride solution to obtain an aqueous solution containing copper values;
(2) contacting the aqueous leach solution from stage (1) with a solution in a water-immiscible organic solvent of the 1-triazole whereby at least a proportion of the copper value is extracted into the organic phase in the form of a halide (or pseudo halide) containing complex of the copper with the 1-triazole;
(3) separating the aqueous phase from the water-immiscible organic solvent phase into which the metal has been extracted;
(4) contacting the resultant organic phase with an aqueous strip solution which is water or which contains a reduced concentration of halide (or pseudo halide) ion or copper whereby the halide (or pseudohalide) containing complex of copper with the 1-triazole is rendered unstable and at least a proportion of the copper transfers into the aqueous strip solution; and
(5) recovering the purified copper values from the aqueous strip solution, for example by electrowinning.

The extraction process of the present invention may be represented by an equation such as the following:

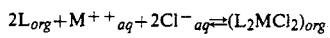

where M is a divalent metal ion such as copper or zinc.

This equation is a grossly oversimplified representation of a very complex process and is not to be taken as in any way limiting the scope of the present invention, but it serves to illustrate the formation of a neutral organic phase complex of the divalent metal and the extractant (L) which is believed to predominate in the process of the present invention. The equation illustrates the reversible nature of the extraction, whereby the complex of the metal and the extractant in the organic phase can be stripped to return the purified and concentrated metal ion into the aqueous phase. Stripping may take place for example on contact of the organic phase containing the metal/extractant complex with water or with the aqueous solution from the metal recovery (for example electrowinning) stage which is depleted in the metal and in the halide ion.

Since the leach solution contains high levels of iron, it is clearly important that the extractant should show good selectivity for copper over iron. Of particular importance to ensure high purity of the product in the recovery of a metal such as copper from its ores is a good selectivity for copper in the presence of silver and other extractable constituents of the ore. The 1-triazole extractants of the present invention generally show excellent selectivity for copper over typical metals which may be present in sulphur containing copper ores.

A further property which is of importance for an extractant in the process of the present invention is the absence of significant protonation by the acidic leach liquor. Such protonation may be represented by an equation such as:

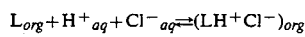

where L is the extractant. Such protonation of the ligand carries hydrochloric acid into the organic phase and builds up an excessive chloride ion concentration on the strip side. We have found that the 1-triazole reagents of the present invention generally show an exceptionally low acid transfer for a given concentration of copper, chloride ion and acid.

As illustrated by the Examples, the extractants of the present invention provide a range of properties so that the optimum extractant may be selected for a given leach solution. The extractants provide a range of extractant "strengths" such that a "strong" extractant has a high affinity for the metal which is naturally offset by a greater difficulty in stripping the reagent to recover the metal. In addition, such "strong" extractants tend to have a high affinity for acid. Thus a "strong" extractant, for example 1-alkyl-1,2,4-triazoles such as 1-(2'-hexyldecyl)-1,2,4-triazole of Example 11 are used most effectively in removing copper from dilute solutions low in chloride ion concentration where its high affinity for copper is of advantage. In solutions having a high concentration of acid and chloride ion, the ligand would tend to transfer an unacceptably high level of acid and would be unnecessarily difficult to strip.

For the leach solutions more commonly encountered in practice, we have found that acyl derivatives such as those illustrated in Examples 4, 5, 6, 9 and 10 and alkoxycarbonyl derivatives such as those illustrated in Examples 1, 2, 3, and 16 show an appropriate "strength" combined with an excellent resistance to acid transfer.

A further property which must be considered in selecting the optimum extractant for a given leach solution is the hydrolytic stability of the extractant. It will be appreciated that in commercial practice the extractant is not used once only, but is recycled between the extraction and strip stages. The inevitable losses are then made up periodically by the addition of fresh reagent. All reagents degrade to a greater or lesser extent and this does not of itself affect the utility of the extractant. However, If a reagent has a particularly low hydrolytic stability, the quantities of fresh reagent required may represent a commercial disadvantage in the treatment of aggressive leach solutions which are high in acid and chloride ion and which promote the degredation of the reagent. 1-alkyl triazoles generally show good hydrolytic stability and of the acyl and alkoxycarbonyl derivatives, those having a high degree of branching at the positions in the vicinity of the carbonyl group in formula (2) (for example those illustrated in Examples 5, 6, 10, 16, 17, 18 and 19) generally show a superior resistance to hydrolysis. Vinyl linked triazoles (formula (7)—and in particular vinyl linked triazoles of formula (7) having an electron withdrawing substituent $S_1$ (for example the extractant of Example 23) show an excellent balance of good hydrolytic stability and a "strength" of reagent adapted to treat leach solutions frequently met in commercial practice.

Examples of suitable water-immiscible organic solvents are aliphatic, aromatic and alicyclic hydrocarbons, chlorinated hydrocarbons such as perchloroethylene, trichloroethane and trichloroethylene. Mixtures of solvents may be used. Especially preferred in conventional hydrometallurgical practice are mixed hydrocarbon solvents such as high boiling, high flash point petroleum fractions (for example kerosene) with varying aromatic content. In general, hydrocarbon solvents having a high aromatic content, for example AROMASOL H which consists essentially of a mixture of trimethylbenzenes and is commercially available from Imperial Chemical Industries PLC (AROMASOL is a trade mark) or SOLVESSO 150 commercially available from Esso (SOLVESSO is a trade mark), provide a higher solubility for the extractant and its metal complex, whilst kerosene having a relatively low aromatic content, for example ESCAID 100 which is a petroleum distillate comprising 20% aromatics, 56.6% paraffins and 23.4% naphthalenes commercially available from Esso (ESCAID is a trade mark) may in certain cases improve the hydrometallurgical performance of the extractant. Factors influencing the solubility of the extractant and its metal complex are complicated, but in general extractants having highly branched substituents and/or an isomeric mixture of substituents have comparatively high solubility. In general, the 1-triazole compounds of the present invention are relatively easy to solubilise in non-polar solvents. The concentration of the extractant in the water-immiscible organic solvent may be chosen to suit the particular leach solution to be treated. Typical values of extractant concentration in the organic phase are between about 0.1 to 2 Molar, and an especially convenient range is from 0.2 to 1.0 Molar in the organic solvent.

Certain triazoles for use in the present invention are novel compounds and the present invention includes such novel compounds.

The invention is illustrated by the following Examples in which all parts and percentages are by weight unless otherwise stated.

EXAMPLE 1

2-Hexyldecyl chloroformate was prepared by adding 2-hexyldecanol (540 g) during 3 hours to liquid phosgene (500 g) which was refluxing below a condenser cooled with a mixture of solid carbon dioxide and acetone. After addition was complete the mixture was stirred for 30 minutes, and excess phosgene was then allowed to evaporate into a scrubbing device charged with 20% aqueous sodium hydroxide. The last traces of phsogene were removed by bubbling nitrogen through the liquid product while it was heated to 120°.

2-Hexyldecyl chloroformate (90 g) was added during 30 minutes to a stirred suspension of potassium carbonate (41 g), and 1,2,4-triazole (21 g) in acetone (350 ml). During addition the temperature of the reaction mixture rose from ambient (22°) to 40°. The mixture was stirred for 16 hours and then poured into water (750 ml) and extracted with toluene. The toluene solution was distilled giving 1-(2'-hexyldecyloxycarbonyl)-1,2,4-triazole (67.1 g), b.p. 165°-175° at 0.4 mm of mercury.

The ability of this compound to extract copper from aqueous solutions containing chloride ion was investigated by the following general method:

An aqueous solution was prepared which was 0.1M in cupric chloride (6.35 gpl copper), and 0.1M in hydrochloric acid and which contained 250 gpl of calcium chloride dihydrate. This solution was then agitated for 1.5 minutes with an equal volume of a solution which was a 0.2M solution of the extractant in AROMASOL H. The layers were allowed to separate and settle, and were separately analysed for copper content. The transfer of copper from the aqueous to the organic phase was calculated as the percentage of the ligand taken up as the copper complex (assuming the complex $L_2CuCl_2$). The transfer of hydrochloric acid from the aqueous solution into the organic solution was calculated as the percentage of ligand that was protonated. The test was repeated using different molarities of hydrochloric acid and different concentrations of calcium chloride. The results are presented in Table 1. The results show that the ligand has good affinity for copper combined with excellent freedom from transfer of acid even at high chloride ion/acid concentrations. On other occasions SOLVESSO 150 or ESCAID 100 (as indicated in Table 1) were used as solvents in place of AROMASOL H.

EXAMPLE 2

Isooctadecyl chloroformate was prepared from isooctadecanol and reacted with 1,2,4-triazole by the methods described in Example 1 to give 1-(isooctadecyloxycarbonyl)-1,2,4-triazole, b.p. 160°-165° at 0.2 mm of mercury. This compound was evaluated as an extractant for copper using the procedure of Example 1 and the results are presented in Table 1.

EXAMPLE 3

2-Octyldodecyl chloroformate was prepared from 2-octyldodecanol and reacted with 1,2,4-triazole by the methods described in Example 1 to give 1-(2'-octyldodecyloxycarbonyl)-1,2,4-triazole, b.p. 190°-210° at 0.3 mm of mercury. This compound was evaluated as an extractant for copper using the procedure of Example 1 and the results are presented in Table 1.

EXAMPLE 4

2-Hexyldecanoic acid was prepared as follows:

Concentrated sulphuric acid (100 g) was diluted with water (750 ml) and this solution was cooled to room temperature and added to a solution of 2-hexyldecanol (242 g) in methylene chloride (600 ml). The solutions were stirred together beneath a reflux condenser and solid potassium permanganate was added in portions during 5 hours so as to maintain gentle boiling of the methylene chloride. The mixture was filtered to remove precipitated manganese dioxide, and the organic layer was separated and washed with water. The solvent was distilled leaving 2-hexyldecanoic acid (222 g) as a nearly colourless oil.

The acid was not further purified but was converted into 2-hexyldecanoyl chloride as follows. The acid was dissolved in toluene (200 ml) and dimethylformamide (5 ml) was added as a catalyst. This solution was stirred and boiled under reflux while thionyl chloride (160 g) was added dropwise during 2 hours. Stirring and heating were continued for a further 2 hour period and then the condenser was reset for collection, and the toluene and excess thionyl chloride were distilled. The residue was then distilled under reduced pressure yielding 2-hexyldecanoyl chloride (161 g) b.p. 118°-124° at 0.45 mm of mercury.

2-Hexyldecanoyl chloride (25 g) was added during 10 minutes to a stirred solution of 1,2,4-triazole (14 g) and pyridine (10 ml) in acetone (50 ml). During addition the temperature rose from 20° to 38°. The mixture was drowned into water and extracted with toluene, and the toluene solution was washed with water and then distilled yielding 1-(2'-hexyldecanoyl)-1,2,4-triazole (33 g), b.p. 156°-160° at 0.15 mm of mercury. This compound was evaluated as an extractant for copper using the procedure of Example 1 and the results are presented in Table 1.

EXAMPLE 5

Following the procedures of Example 4, isooctadecanol was used to prepare isooctadecanoic acid and thence isooctadecanoyl chloride (b.p. 120° C. at 1.0 mm of mercury pressure) and finally 1-isooctadecanoyl-1,2,4-triazole (b.p. 136°-140° C. at 0.15 mm of mercury pressure). This compound was evaluated as an extractant for copper using the procedure of Example 1 and the results are presented in Table 1.

EXAMPLE 6

Following the procedures of Example 4, 2-octyldodecanol was used to prepare 2-octyldodecanoic acid and thence 2-octyldodecanoyl chloride (b.p. 160°-168° C. at 0.6 mm of mercury pressure) and finally 1-(2'-octyldodecanoyl)-1,2,4-triazole, (b.p. 160°-170° at 0.2 mm of mercury). This compound was evaluated as an extractant for copper using the procedure of Example 1 and the results are presented in Table 1.

EXAMPLE 7

VERSETIC ACID is a commercial mixture (Shell Chemical Co.) of aliphatic tertiary carboxylic acids each containing ten carbon atoms, in which one of the three substituents at the alpha-carbon atom is predominantly the methyl group. Versetic acid was converted into its acid chloride (b.p. 102°-110° at 15 mm of mercury), and thence into a mixture of branched 1-tert.decanoyl-1,2,4-triazoles (b.p. 90°-105° at 0.1 mm of mercury) by the procedures of Example 4. This mixture was evaluated as an extractant for copper using the procedure of Example 1 and the results are presented in Table 1. The results show that the mixture has good affinity for copper combined with excellent freedom from transfer of acid even at high chloride ion concentrations. When tested at the higher acid concentrations (1.0M HCl), some hydrolytic instability was noted.

EXAMPLE 8

Isooctadecanoyl chloride prepared as described in Example 5 (20.2 g) was stirred and heated to 100° and illuminated with a tungsten lamp (100 watts) whilst bromine (10.7 g) was added dropwise during 1.5 hours. Heating and stirring under illumination were continued and further additions of bromine were made until after 10 hours and the addition of a further 6 g of bromine, 95% of the starting material was shown by gas chromatography to be completely reacted. Excess bromine and hydrobromic acid were removed by applying partial vacuum (20 mm of mercury) to the heated liquid. The 2-bromoisooctadecanoyl chloride thus obtained was cooled and treated with 1,2,4-triazole (9.0 g) and drowned into water and extracted with petroleum ether (b.p. 60°-80°). The organic solution was separated and washed with aqueous hydrochloric acid (2M) and water, and the solvent was distilled leaving 1-(2'-bromoisooctadecanoyl)-1,2,4-triazole (25.3 g) as a pale brown oil. The nuclear magnetic resonance spectrum of the product as a solution in deuterated chloroform was compared with that of the product of Example 5, confirming that absorption at delta 3.4 ppm from tetramethylsilane, associated with a proton in the 2'-position of the side chain, had vanished. This compound was evaluated as an extractant for copper by the procedure of Example 1 and the results are presented in Table 1. The results show that the compound is a slightly "weaker" ligand than the products of Examples 1-7, and that it transfers only a small amount of acid.

EXAMPLE 9

Phthalic anhydride (52 g) was added to 2-octyldodecanol (90 g) and the mixture was stirred and heated to 140° for 1 hour and then rapidly to 190° for 10 minutes and then cooled. The mixture was filtered to remove excess phthalic anhydride and any phthalic acid formed, yielding 2-(2'-octyldodecyloxycarbonyl)benzoic acid (110 g).

Thionyl chloride (15 ml) and dimethylformamide (0.1 ml = were added to the acid described above (45 g) and the mixture was stirred and heated to 90° for 30 minutes. The pressure was then reduced to 20 mm of mercury so that excess thionyl chloride distilled. The residue which is 2-(2'-octyldodecyloxycarbonyl)benzoyl chloride was not isolated but was treated with 1,2,4-triazole (12 g) and pyridine (15 ml) at ambient temperature and the mixture was stirred for 30 minutes and then poured into water (500 ml) and extracted with toluene. The toluene solution was washed with aqueous hydrochloric acid (2M) and water and the solvent was distilled yielding 1-[2'-(2''-octyldodecylcarbonyloxy)benzoyl]-1,2,4-triazole (45.6 g). This compound was evaluated as an extractant for copper by the procedure of Example 1 and the results are presented in Table 1.

EXAMPLE 10

Tetrachlorophthalic anhydride was treated first with isooctadecanol, and then with thionyl chloride and dimethylformamide, and then with 1,2,4-triazole and pyridine by the procedures of Example 9, so as to give 1-[2'-(isooctadecylcarbonyloxy)-3',4',5',6'-tetrachlorobenzoyl]-1,2,4-triazole having the formula:

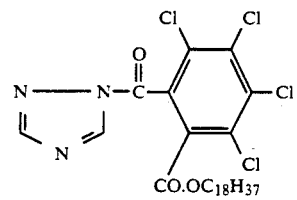

This compound was evaluated as an extractant for copper using the procedure of Example 1 and the results are presented in Table 1.

EXAMPLE 11

1-Bromo-2-hexyldecane was prepared by reacting 2-hexyldecanol with hydrogen bromide gas, or with 47% aqueous hydrogen bromide, according to well known procedures. The crude product was purified by distillation, b.p. 152°-154° at 18 mm of mercury.

1,2,4-Triazole (10.0 g) and potassium hydroxide (90% strength, 6.0 g) were dissolved in dimethylformamide (50 ml) and this solution was stirred with 1-bromo-2-hexyldecane (30.5 g) and potassium iodide (0.2 g) and heated to 95°-105° for 15 minutes. A further quantity of potassium hydroxide (1.5 g) was then added and stirring and heating were continued for a total of 2 hours. The mixture was then cooled and diluted with water and extracted with petroleum spirit (b.p. 60°-80°) and the organic solution was well washed with water and then distilled. 1-(2'-hexyldecyl)-1,2,4-triazole (23.1 g) was collected as the fraction boiling between 125°-150° at 0.1 mm pressure. This compound was evaluated as an extractant for copper using the procedure of Example 1, and the results are presented in Table 1. The results show that the compound has a very high affinity for copper, and would be best employed in removing copper from dilute solutions low in chloride ion concentration.

EXAMPLE 12

Diisodecyl malonate was prepared by heating diethyl malonate at 160° with an excess of isodecanol in the presence of tetrabutyl titanate, and purified by vacuum distillation, b.p. 165°–170° at 0.6 mm pressure. This compound was reacted with bromine to give diisodecyl bromomalonate by adapting the procedure given in "Organic Synthesis, Collected Volume 1" at page 245.

1,2,4-Triazole (43.1 g) and diisodecyl bromomalonate (232 g) were stirred with acetone (250 cm³), and anhydrous potassium carbonate (83.4 g) was added in portions during 1 hour so that the temperature did not rise above 30°. After stirring for 1 hour further, the solution was filtered, and the acetone was distilled under reduced pressure. The residue was dissolved in toluene (250 cm³) and well washed with N.hydrochloric acid solution and with 5% sodium carbonate solution and with water. The toluene was distilled under reduced pressure leaving a reddish oil which consists essentially of 1-[bis(isodecyloxycarbonyl)methyl]-1,2,4-triazole of formula:

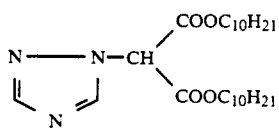

The purity as determined by titration with perchloric acid in glacial acetic acid/acetic anhydride was 86%. This compound was evaluated as an extractant for copper using the procedure of Example 1 and the results are presented in Table 1.

EXAMPLE 13

1-[bis(isodecyloxycarbonyl)methyl]-1,2,4-triazole (51.8 g, 86% strength) was stirred and boiled under reflux at 78° with carbon tetrachloride (100 cm³) whilst bromine (16.0 g) was added slowly beneath the liquid surface during 30 minutes. Stirring and heating at 78°–80° was continued for a further period of 2 hours, the extent of bromination being followed by disappearance of the resonance due to the methine proton at delta=5.8 ppm from tetramethylsilane in the nmr spectrum. The solution was then cooled, washed with dilute aqueous sodium sulphite solution and with water, and the solvent was distilled yielding 57.2 g of 1-[1',1'-bis-(isodecyloxycarbonyl)-1'-bromomethyl]-1,2,4-triazole of strength 76% as measured by non-aqueous titration with perchloric acid. This compound was evaluated as an extractant for copper using the procedure of Example 1 and the results are presented in Table 1.

EXAMPLE 14

1-[bis(isodecyloxycarbonyl)methyl]-1,2,4-triazole, which is the product of Example 12 (15.6 g), was dissolved in carbon tetrachloride (20 ml). Phosphorus trichloride (3 drops) was added and the solution was stirred and heated at 60° whilst a slow stream of chlorine was bubbled through it for 1 hour. The solution was then cooled, washed with aqueous sodium sulphite solution and with water, and the solvent was distilled under reduced pressure yielding 1-[bis(isodecyloxycarbonyl)chloromethyl]-1,2,4-triazole (12.9 g), which had a purity of 82.4% as measured by non-aqueous titration with perchloric acid. This compound was evaluated as an extractant for copper by the procedure of Example 1 and the results are presented in Table 1.

EXAMPLE 15

Isooctadecyl chloroacetate (b.p. 138°–146°, 0.2 mm of mercury pressure) was prepared by reacting chloracetyl chloride with isooctadecanol. By the procedure of Example 11, this compound was reacted with 1,2,4-triazole to give 1-(isooctadecyloxycarbonylmethyl)-1,2,4-triazole of 84% strength by non-aqueous titration with perchloric acid. This compound was evaluated as an extractant for copper by the procedure of Example 1 and the results are presented in Table 1.

EXAMPLE 16

3,9-Diethyl-6-tridecanol (a secondary alcohol) was reacted with phosgene by the procedure of Example 1 to form the corresponding sec alkyl chloroformate, and this compound was reacted with 1,2,4-triazole, using pyridine as acid binder and solvent, to yield 1-[3,9-diethyl-6-tridecyloxycarbonyl]-1,2,4-triazole of formula:

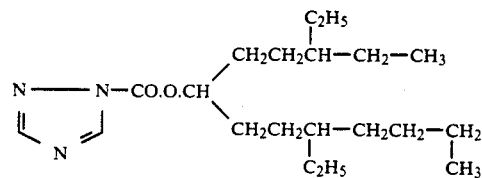

The compound was evaluated as an extractant for copper by the procedure of Example 1 and the results are presented in Table 1.

TABLE 1

| Product of Ex. No. | Solvent | HCl (Molarity) | CaCl$_2$.2H$_2$O (g/l) | % Uptake from 0.1M CuCl$_2$ Copper | HCl |
|---|---|---|---|---|---|
| 1 | AROMASOL H | 0.1 | 250 | 47 | 0 |
|   |   | 0.1 | 700 | 74 | 0 |
|   |   | 1.0 | 250 | 58 | 0 |
|   |   | 1.0 | 700 | 77 | 0 |
| 2 | SOLVESSO 150 | 0.1 | 250 | 47 | 0 |
|   |   | 0.1 | 700 | 74 | 1 |
|   |   | 1.0 | 250 | 58 | 0 |
|   |   | 1.0 | 700 | 78 | 1 |
| 3 | SOLVESSO 150 | 0.1 | 250 | 47 | 0 |
|   |   | 0.1 | 700 | 77 | 1 |
|   |   | 1.0 | 250 | 58 | 0 |
|   |   | 1.0 | 700 | 78 | 1 |
| 4 | AROMASOL H | 0.1 | 250 | 40 | 0 |
|   |   | 0.1 | 700 | 72 | 0 |
|   |   | 1.0 | 250 | 52 | 0 |

TABLE 1-continued

| Product of Ex. No. | Solvent | HCl (Molarity) | $CaCl_2.2H_2O$ (g/l) | % Uptake from 0.1M $CuCl_2$ | |
|---|---|---|---|---|---|
| | | | | Copper | HCl |
| | | 1.0 | 700 | 73 | 0 |
| 5 | SOLVESSO 150 | 0.1 | 250 | 38 | 0 |
| | | 0.1 | 700 | 71 | 0 |
| | | 1.0 | 250 | 49 | 0 |
| | | 1.0 | 700 | 73 | 0 |
| 5 | ESCAID 100 | 0.1 | 250 | 32 | <1 |
| | | 0.1 | 700 | 69 | <1 |
| | | 1.0 | 250 | 41 | <1 |
| | | 1.0 | 700 | 73 | 1 |
| 6 | SOLVESSO 150 | 0.1 | 250 | 28 | 0 |
| | | 0.1 | 700 | 71 | 0 |
| | | 1.0 | 250 | 52 | 0 |
| | | 1.0 | 700 | 74 | <1 |
| 7 | AROMASOL H | 0.1 | 250 | 40 | 0 |
| | | 0.1 | 500 | 62 | 0 |
| | | 0.1 | 700 | 74 | 0 |
| 8 | SOLVESSO 150 | 0.1 | 250 | 9 | 1 |
| | | 0.1 | 700 | 49 | 2 |
| | | 1.0 | 250 | 21 | 2 |
| | | 1.0 | 700 | 53 | 3 |
| 9 | SOLVESSO 150 | 0.1 | 250 | 29 | 2 |
| | | 0.1 | 700 | 70 | 2 |
| | | 1.0 | 250 | 49 | 2 |
| | | 1.0 | 700 | 73 | 3 |
| 10 | SOLVESSO 150 | 0.1 | 250 | 6 | 4 |
| | | 0.1 | 700 | 55 | 4.5 |
| | | 1.0 | 250 | 16 | 5 |
| | | 1.0 | 700 | 55 | 4.5 |
| 10 | ESCAID 100 | 0.1 | 250 | 10 | 5 |
| | | 0.1 | 700 | 47 | 7 |
| | | 1.0 | 250 | 18 | 7 |
| | | 1.0 | 700 | 51 | 8 |
| 11 | AROMASOL H | 0.1 | 250 | 96 | 0 |
| | ESCAID 100 | 1.0 | 250 | 98 | 4 |
| | | 1.0 | 700 | 88 | 91 |
| 12 | SOLVESSO 150 | 0.1 | 250 | 77 | 3 |
| | | 0.1 | 700 | 84 | 4 |
| | | 1.0 | 250 | 89 | 4 |
| | | 1.0 | 700 | 91 | 16 |
| 13 | SOLVESSO 150 | 0.1 | 250 | 55 | 3 |
| | | 0.1 | 700 | 88 | 3 |
| | | 1.0 | 250 | 67 | 3 |
| | | 1.0 | 700 | 85 | 5 |
| 14 | SOLVESSO 150 | 0.1 | 250 | 49 | 2.5 |
| | | 1.0 | 700 | 86 | 4 |
| 15 | SOLVESSO 150 | 0.1 | 250 | 94 | 2 |
| | | 0.1 | 700 | 99 | 11 |
| | | 1.0 | 250 | 96 | 5 |
| | | 1.0 | 700 | 88 | 62 |
| 16 | SOLVESSO 150 | 0.1 | 250 | 47 | 0 |
| | | 1.0 | 700 | 88 | 1 |

EXAMPLE 17

2-Methyl-7-ethyl-4-undecanol (a secondary alcohol) was reacted with phosgene by the procedure of Example 1 to form the corresponding sec alkyl chloroformate, and this compound was reacted with 1,2,4-triazole using pyridine as acid binder and solvent, to yield 1-[2-methyl-7-ethyl-4-undecyloxycarbonyl]-1,2,4-triazole of formula:

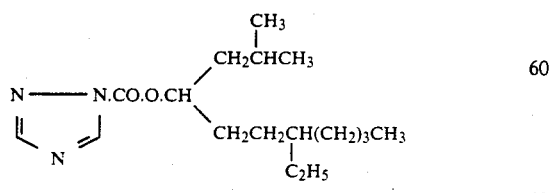

The compound was evaluated as an extractant for copper by the procedure of Example 1 and the results are presented in Table 2.

EXAMPLE 18

8-Ethyl-2,2,4-trimethyl-6-dodecanol (b.p. 86°-90° at 0.15 mm of mercury pressure) was prepared by reacting 1-bromo-2-ethylhexane and 3,5,5-trimethylhexanol with lithium in tetrahydrofuran at 0° to −10° according to the general method of Pearce, Richards and Scilly (J. Chem. Soc., Perkin I, 1655, 1972). This compound was converted, by way of the chloroformate, into 1-[8-ethyl-2,2,4-trimethyl-6-dodecyloxycarbonyl]-1,2,4-triazole of formula:

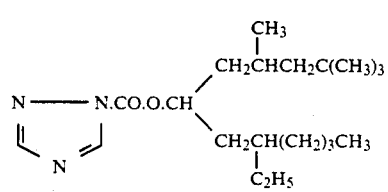

The compound was evaluated as an extractant for copper by the procedure of Example 1 and the results are presented in Table 2.

EXAMPLE 19

2,2,4,9,11,11-Hexamethyl-6-dodecanol (b.p. 104°–110° at 0.18 mm of mercury pressure) was prepared by reacting 1-bromo-3,5,5-trimethylhexane with 3,5,5-trimethylhexanal and converted into 1-[2,2,4,9,11,11-hexamethyl-6-dodecyloxycarbonyl]-1,2,4-triazole of formula:

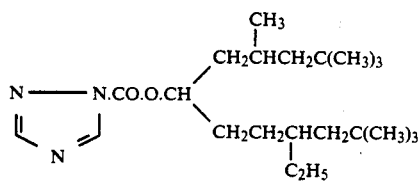

following the procedures of Example 18. This compound was evaluated as an extractant for copper by the procedure of Example 1 and the results are presented in Table 2.

EXAMPLE 20

The procedure of Example 10 but using 3,6-dichlorophthalic anhydride as starting material was used to prepare 1-[-2'-isooctadecylcarbonyloxy)-3',6'-dichlorobenzoyl]-1,2,4-triazole having the formula:

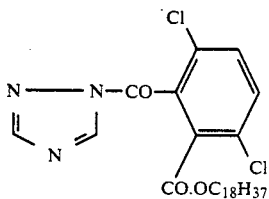

This compound was evaluated as an extractant for copper by the procedure of Example 1 and the results are presented in Table 2.

EXAMPLE 21

A mixture of cis-3-bromoacrylic acid (11.3 g), isooctadecanol (40.5 g), p-toluenesulphonic acid (2 g) and toluene (50 ml) was stirred and boiled under reflux below a Dean-Stark trap of volume 15 ml for 3 hours. The mixture was then cooled and extracted with petroleum ether (b.p. 60°–80°), and the petroleum layer was washed with water and distilled yielding 14.5 g of isooctadecyl cis-2-bromo-acrylate, b.p. 130°–150° at 0.05 mm of mercury pressure. This ester (14.0 g) was added to a stirred solution of 1,2,4-triazole (4.5 g) in dimethylformamide (30 ml) containing 85% potassium hydroxide pellets (3.5 g) and the mixture was heated for 10 minutes at 70° and then cooled. Butyl acetate (40 ml) was then added and the mixture reheated at 70° for a further 10 minutes. The mixture was cooled, diluted with petroleum ether (100 ml) and well washed with water. The petroleum solution was separated and distilled yielding 7.7 g of isooctadecyl 3-(1,2,4-triazol-1-yl)acrylate, b.p. 180°–185° at 0.05 mm of mercury pressure. The nmr spectrum of this compound indicated that essentially only one geometrical distribution of groups at the olefinic double bond was present, and the J coupling between the olefinic protons of about 13 Hertz tends to suggest that this has the trans-structure depicted.

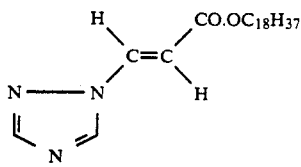

This compound was evaluated as an extractant for copper by the procedure of Example 1 and the results are presented in Table 2.

EXAMPLE 22

A mixture of cis and trans ethyl 3-chlorocrotonate prepared as described by A. Holy (Coll. Czech. Chem. Commun. 39, 3183, 1974) (34.2 g) was added to a stirred suspension of 1,2,4-triazole (15.1 g) and potassium carbonate (21 g) in acetone (200 ml) and dimethyl formamide (50 ml) and the mixture was boiled under reflux (58°–60°). After 18 hours gas chromatography showed that about 50% reaction had occurred. Potassium hydroxide (5.2 g of 85% pellets) were added, and reflux was continued for 2 hours. The mixture was cooled and filtered and diluted with an equal volume of water and saturated with sodium chloride and then extracted with petroleum ether. The petroleum layer was separated and the solvent was distilled under reduced pressure leaving a solid which was recrystallised from petroleum ether (1000 ml) yielding ethyl 3-(1,2,4-triazol-1-yl) crotonate as a white solid m.p. 85°–86° (15.8 g). Nuclear Overhauser Enhancement experiments indicated the methyl group and the hydrogen atom to be trans to one another.

This ester (13.6 g) was stirred and heated under an atmosphere of nitrogen with isooctadecanol (50 g) and tetrabutyl titanate (0.5 ml) for 10 hours at 135° and finally for 2 hours at 160°. The mixture was then distilled yielding isooctadecyl 3-(1,2,4-triazol-1-yl)crotonate as a viscous oil, b.p. 190°–195° at 0.1 mm of mercury pressure. The compound is believed to have the geometry depicted in the formula:

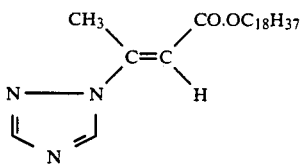

This compound was evaluated as an extractant for copper by the procedure of Example 1 and the results are presented in Table 2.

EXAMPLE 23

Bromomaleic anhydride (19.5 g), isodecanol (69.5 g) p-toluene sulphonic acid (2 g) and toluene (70 ml) were stirred and boiled under reflux below a Dean-Stark trap of volume 15 ml for 2.5 hours. The solution was then cooled with petroleum ether and the petroleum ether solution was washed with water. The solvent and excess isodecanol were distilled under reduced pressure, finally at 100°/0.2 mm of mercury pressure, leaving the bis(isodecyl)ester of bromomaleic acid (56 g) as an oil with an estimated purity by gas chromatography of 96%.

This ester (59.5 g), 1,2,4-triazole (19 g) and acetone (100 ml) were stirred together at room temperature and potassium carbonate (25 g) was added evenly in small portions during 1 hour. After a further 3½ hours the solution was filtered and then diluted with water and extracted with petroleum ether. The solvent was distilled from the petroleum solution giving an intermediate (63.5 g) believed to have the structure

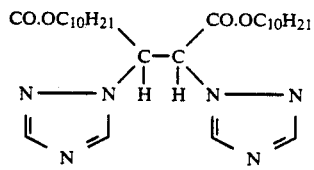

The intermediate (32 g) was heated with acetic anhydride and zinc chloride (0.1 g) for 3 hours at 120°. The mixture was cooled and extracted with petroleum ether and the petroleum solution was well washed with water, then separated and dried with magnesium sulphate. The solvent was distilled under reduced pressure, yielding isodecyl 3-isodecyloxycarbonyl-3-[1,2,4-triazol-1-yl]acrylate (27.8 g). The nmr spectrum of this compound indicates that both cis and trans isomers were present.

This compound was evaluated as an extractant for copper by the procedure of Example 1 and the results are presented in Table 2.

Together with the products of Examples 22 and 21, this compound showed very high hydrolytic stability, even at elevated temperature. The product of this example is particularly valuable because in addition to this feature, as shown by the results in Table 2, it shows little acid transfer even from the strongly acidic feed solution of high chloride concentration.

each ligand (0.2 Molar) in SOLVESSO 150 was contacted by shaking for 1 minute with an equal volume of an aqueous solution which was 0.1 Molar in copper (II) chloride and 0.1 Molar in hydrochloric acid, and contained 700 g per liter of calcium chloride dihydrate. The organic solution was separated and then stripped by shaking for one minute with an equal volume of water, which was separated. The organic solution was further stripped by shaking with a second equal volume of water. The amounts of copper which were originally extracted into the organic solution, and subsequently removed at each stripping stage are listed below.

| Ligand | Copper (grams per liter) | | |
|---|---|---|---|
| | Originally extracted | Recovered at 1st stripping | Recovered at 2nd stripping |
| Product of Ex. 18 | 5.18 | 5.08 | 0.06 |
| Product of Ex. 20 | 3.56 | 3.49 | 0.06 |
| Product of Ex. 23 | 5.56 | 5.21 | 0.32 |

EXAMPLE 25

An aqueous solution typical of the concentrated feed solution obtainable by leaching a complex sulphide ore with ferric chloride solution was prepared by dissolving hydrochloric acid and the metal chlorides listed below in water to give the metal concentrations listed in the first row of Table 3. The concentration of hydrochloric acid in this solution was 0.5 molar and the total concentration of chloride was 10 molar. Metal chlorides: copper (II), iron (II), zinc (II), lead (II), antimony (III), arsenic (III), tin (II), cadmium (II). Metal nitrate: silver (I).

A 0.5 Molar solution in ESCAID 100 of the extractant of Example 5 (2.5 parts by volume) was contacted by shaking for 1.5 minutes with the aqueous feed solution (1 part by volume). The organic solution was then separated and analysed for metals content, with the results listed in of Table 3.

TABLE 2

| Product of Ex. No. | Solvent | HCl (Molarity) | CaCl₂.2H₂O (g/l) | % Uptake from 0.1M CuCl₂ | |
|---|---|---|---|---|---|
| | | | | Copper | HCl |
| 17 | SOLVESSO 150 | 0.1 | 250 | 46 | 0 |
| | | 0.1 | 700 | 87 | 0 |
| | | 1.0 | 250 | 61 | 0 |
| | | 1.0 | 700 | 93 | 0 |
| 18 | SOLVESSO 150 | 0.1 | 250 | 37 | 0 |
| | | 0.1 | 700 | 80 | 0 |
| | | 1.0 | 250 | 51 | 0 |
| | | 1.0 | 700 | 82 | 0 |
| 19 | SOLVESSO 150 | 0.1 | 250 | 43 | 0 |
| | | 0.1 | 700 | 86 | 0 |
| | | 1.0 | 250 | 58 | 0 |
| | | 1.0 | 700 | 88 | 0.5 |
| 20 | SOLVESSO 150 | 0.1 | 250 | 12 | 0 |
| | | 0.1 | 700 | 55 | 0 |
| | | 1.0 | 250 | 24 | 0 |
| | | 1.0 | 700 | 61 | 0.5 |
| 21 | SOLVESSO 150 | 0.1 | 250 | 76 | 0 |
| | | 0.1 | 700 | 93 | 0 |
| | | 1.0 | 700 | 93 | 7 |
| 22 | SOLVESSO 150 | 0.1 | 250 | 67 | 0 |
| | | 0.1 | 700 | 91 | 0 |
| | | 1.0 | 250 | 75 | 0 |
| | | 1.0 | 700 | 92 | 4 |
| 23 | SOLVESSO 150 | 0.1 | 250 | 65 | 0 |
| | | 0.1 | 700 | 86 | 0 |
| | | 1.0 | 250 | 73 | 0.5 |
| | | 1.0 | 700 | 92 | 2 |

EXAMPLE 24

This example demonstrates the efficient stripping properties of the ligands of the invention. A solution of By way of comparison, the evaluation was exactly repeated using a 0.5 Molar solution in ESCAID 100 of the extractant of Example 11 of European Patent Publication No. 57 797 and the comparative results are shown in Table 3.

TABLE 3

| Solution | Metal Concentration (g. per l or parts per million) | | | | | | | | |
|---|---|---|---|---|---|---|---|---|---|
| | Cu gpl | Fe gpl | Zn gpl | Pb gpl | Sb ppm | As ppm | Sn ppm | Cd ppm | Ag ppm |
| Aqueous feed | 50 | 150 | 18 | 3.0 | 128 | 92 | 117 | 175 | 55 |
| 1-isooctadecanoyl-1,2,4-triazole (Product of Ex. 5) | 13.9 | 0.04 | 0.04 | 0.007 | 11 | 1.5 | 1.5 | <0.25 | 0.25 |
| COMPARISON Diisodecylpyridine-3,5-dicarboxylate (Example 11 of EP 57797) | 14.2 | 0.75 | 0.13 | 0.18 | 14 | 8.5 | 28 | 14 | 0.2 |

We claim:

1. A triazole which is 1-(alkyl)oxycarbonyl or a 1-alkylcarbonyl-1,2,4-triazole of formula (4) or (5) respectively:

$$N\text{———}N-\overset{\overset{\displaystyle O}{\|}}{C}-OR_2 \quad (4)$$

or $$N\text{———}N-\overset{\overset{\displaystyle O}{\|}}{C}-R_3 \quad (5)$$

wherein $R_2$ and $R_3$ respectively are branched chain alkyl groups containing from 9 to 24 carbon atoms.

2. A 1-substituted-1,2,4 triazole selected from the group consisting of
1-[3,9-diethyl-6-tridecyloxycarbonyl]1,2,4-triazole;
1-[2-methyl-7-ethyl-4-undecyloxycarbonyl]1,2,4-triazole;
1-[-ethyl-2,2,4-trimethyl-6-dodecyloxycarbonyl]-1,2,4-triazole;
1-[2,2,4,9,11,11-hexamethyl-6-dodecyloxycarbonyl]1,2,4-triazole;
1(2'-hexyldecyloxycarbonyl)-1,2,4-triazole;
1-(isooctadecyloxycarbonyl)-1,2,4-triazole;
1-(2'-octyldodecyloxycarbonyl)-1,2,4-triazole;
1-(2'hexyldecanoyl)-1,2,4-triazole;
1-isooctadecanoyl-1,2,4-triazole;
1-(2'-octyldodecanoyl)-1,2,3-triazole and branched 1-tert. decanoyl-1,2,4-triazole.

* * * * *